United States Patent [19]

Glabiszewski

[11] Patent Number: 4,529,332
[45] Date of Patent: Jul. 16, 1985

[54] TUBULAR JOINT FOR RECEIVING AND FASTENING TUBULAR SKELETON ELEMENTS OF ARTIFICIAL LIMBS

[75] Inventor: Richard Glabiszewski, Duderstadt, Fed. Rep. of Germany

[73] Assignee: Otto Bock Orthopädische Industrie KG, Duderstadt, Fed. Rep. of Germany

[21] Appl. No.: 486,847

[22] Filed: Apr. 20, 1983

[30] Foreign Application Priority Data

Apr. 21, 1982 [DE] Fed. Rep. of Germany ....... 3214772

[51] Int. Cl.³ .......................... F16D 1/06; A61F 1/04; A61F 1/08
[52] U.S. Cl. .................................... 403/366; 403/362; 403/374; 403/DIG. 9; 623/18; 623/31; 623/38
[58] Field of Search .................... 3/1, 2, 15, 17 R, 21, 3/22; 403/366, 362, 374, 343, DIG. 9

[56] References Cited

U.S. PATENT DOCUMENTS

| | | | |
|---|---|---|---|
| 564,741 | 7/1896 | Dunn | 403/362 |
| 1,074,839 | 10/1913 | Curry | 403/366 X |
| 2,194,800 | 3/1940 | Ley | 403/366 |
| 2,760,800 | 8/1956 | Wekeman | 403/366 |

FOREIGN PATENT DOCUMENTS 214096  4/1924  United Kingdom ................... 3/21

Primary Examiner—Ronald L. Frinks
Attorney, Agent, or Firm—Michael J. Striker

[57] ABSTRACT

A tubular joint for receiving and fastening a tubular element of an artificial limb includes a tubular member having a chamber to receive the tubular element therein and formed with a recess defined by inner walls of the coupling conically inclined towards each other, two clamping grips overhung in the recess, and an adjusting screw insertable into the coupling to press the clamping grips against the tubular element to clamp the latter in the chamber of the coupling.

3 Claims, 2 Drawing Figures

TUBULAR JOINT FOR RECEIVING AND FASTENING TUBULAR SKELETON ELEMENTS OF ARTIFICIAL LIMBS

BACKGROUND OF THE INVENTION

The present invention relates generally to tubular joints for use in prothetic devices. More particularly, the invention relates to a tubular joint for receiving and fastening tube-like skeleton elements of an artificial limb, provided with an adjustable manipulation means for changing an inner diameter of the tubular joint.

Known structures of artificial limbs including tubular skeleton elements have a number of disadvantages. The tubular skeleton elements are usually stably adjustable and cosmetically coated so as to satisfy requirements to artificial limbs.

To connect the tube-like skeleton, element for example to a joint, tubular joints or couplings have been utilized which have been formed with longitudinal slots to receive the ends of respective tubes. A flange portion has been provided at the edge of the longitudinal slot, through which flange a setscrew was extended so that the width of the slot has been changed and adjusted by the setscrew. A decrease in the slot width after the tubular member has been inserted caused a decrease in the inner diameter of the tubular coupling so that the tubular member was clamped in the tubular coupling.

Research which has been conducted with conventional tubular couplings or joints has showed that despite of the fact that conventional couplings could satisfactorily serve for a almost a year they are rather disadvantageous. Since the decrease in the slot width causes a descrease in the inner diameter of the tubular coupling this leads to even further decrease of the inner diameter of the coupling at the free end thereof. Therefore the tube inserted into the coupling will be held substantially at its outermost edge. This will lead to circular sharp loads exerted on the clamped tube which will be loaded by local forces. These loads can cause significant local weakening of the tube after a certain period of time which would affect stability of the tube. This can potentially damage the tube connection, for example a tube connection of the hip joint with the upper shank joint tube, due to a lever ratio and relatively great forces acting on the tube connections. With the use of fiber-reinforced plastics tubes there is a risk of damaging of fiber laminations oriented in the direction of loads exerted on the tubes.

SUMMARY OF THE INVENTION

It is an object of the invention to provide an improved tubular joint for receiving and fastening a tubular element of an artificial limb.

It is a further object of the invention to provide a joint which ensures a reliable fastening of the tubular element without, however, weakening the tubular element clamped in the joint.

These and other objects of the invention are attained by a tubular coupling for receiving and fastening a skeleton tubular element of an artificial limb, comprising a tubular member having a chamber to receive the tubular element therein and further formed with a recess defined by inner walls of the coupling conically inclined towards each other; two clamping grips positioned in said recess, said grips having circular surfaces corresponding to the outer surface of the tubular element to be received in said chamber, and an adjusting screw insertable into the coupling to press against said clamping grips so that said grips abut against said inner inclined walls and said circular surfaces abut against the tubular element received in said chamber to clamp it in position.

The tubular coupling according to the invention ensures a surface-like decrease of the inner cross-section of the tubular member of the coupling by the adjusting screw. The clamping grips may have sufficiently great length so that circular local loads on the clamped tubular element will be prevented from occurrence.

The clamping grips may be positioned in said tubular member so that they are pivotable in the direction of an axis of the tubular member. It is particularly advantageous that the clamping grips are overhung in the recess of the tubular coupling. This can be provided by means of pins which extend through openings of greater diameters than the diameters of the pins which are further inserted into inclined walls of the clamping grips. The difference between the inner diameters of the openings in the tubular member of the coupling and the outer diameter of the pins ensures the possibility of a radial adjustment of the clamping grips.

Preferably the clamping grips are pivotable in the axial direction. This is advantageous because tube allowances can be significantly compensated. Even somewhat conically-shaped tubes can be properly inserted and clamped in the coupling of the invention because they can be adjusted to the chamber of the coupling by overhung tiltable grips. The pivotability of the clamping grips in the axial direction ensures that these grips are in point-line contact with the tubular coupling.

The clamping grip may each have a curved surface corresponding to the respective inclined inner wall of the tubular member, said grips being each connected to the tubular member at a point extending approximately in the middle of the curvature defining said curved surface. The coupling may further include pins connecting said clamping grips to said tubular member, said clamping grips being adjustable in position by a hand manipulation of said adjusting screw.

The clamping grips may each have an inclined surface opposite to said circular surface thereof so that two clamping grips inserted into said recess form a conical surface, said adjusting screw having a conical tip cooperating with said conical surface upon advancing of said screw towards the chamber of the tubular member of the coupling.

Due to the conical-type arrangement of the walls of the clamping grips and the inclined walls of the recess of the tubular member of the coupling it is possible to adjust the position of clamping grips by handle manipulation of the adjusting screw at the height of pivot points of the grips.

Upon advancing movement of the adjusting screw the clamping grips will slide over the inclined inner wall forming the recess in the coupling tubular member. Due to the conical-type arrangement only one adjusting screw is sufficient to provide slidable movement of both clamping grips parallel to each other. It should be noted that the clamping grips will not be essentially tilted or pivoted in the radial direction whereby no local loads will be exerted on the clamped tubes in the axial direction.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DESCRIPTION OF THE PREFERRED EMBODIMENTS

Figure 1:
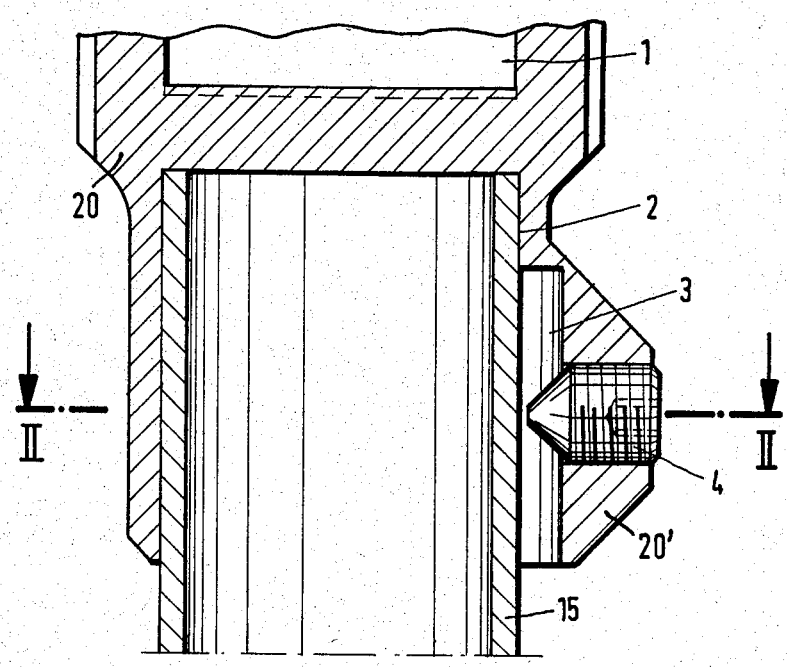
FIG. 1 is an axial sectional view through a tubular coupling according to the invention.
Figure 2:
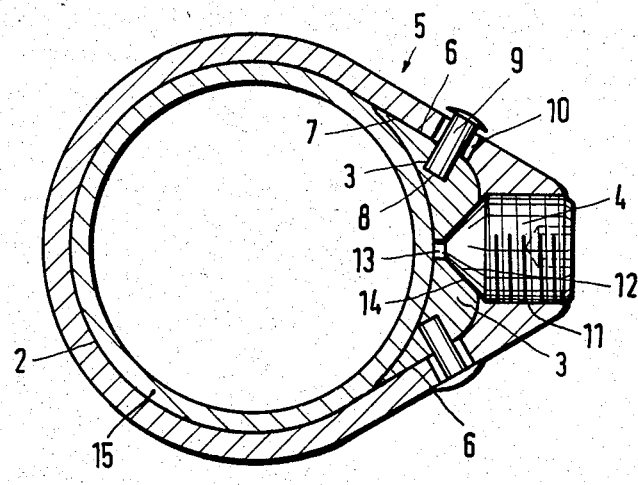
FIG. 2 is a sectional view on line 11—11 of FIG. 1.

A tubular coupling for receiving and fastening a tubular skeleton element of an artificial limb, shown in FIGS. 1 and 2, includes a tube 20 formed with a chamber 1 for securing on the joint element (not shown) and a chamber 2 for receiving therein a tubular member 15.

Chamber 2 which has a substantially circular cross-section is adjustable by means of clamping grips 3 which in turn are adjustable in their radial position by an adjusting setscrew 4. Clamping grips 3 extend approximately along the whole length of chamber 2 which receives tubular member 15.

The structure of the tubular joint according to the invention is clearly seen from FIG. 2. Clamping grips 3 are positioned in a recess 5 provided in the tubular joint. Recess 5 is formed by two inner walls 6 of tubular element 20, which walls extend conically toward each other. Clamping grips 3 have inclined outer surfaces 7 which abut against conical walls 6 constituting recess 5. Inner surfaces or walls 8 of the clamping grips facing toward chamber 2 have somewhat circular cross-sections which define a circular surface into which chamber 2 merges.

Clamping grips 3 are held in their axial postion by setscrew 4 which urges clamping grips 3 against tubular member 15 inserted into chamber 2. Adjusting screw 4 is formed as a hollow screw. In addition the clamping position of grips 3 is ensured by means of rivet-like pins 9. Pins 9 extend through respective through holes 10 formed in conical walls provided in a projection 20' of tubular element 20 of the joint and further into respective openings formed in clamping grips 3. Through holes 10 have greater diameters than those of pins 9.

Adjusting screw or axle 4 is inserted into a threaded bore 11 provided in projection 20' approximately at the half of the height of clamping grips 3. Setscrew 4 has in the preferred embodiment a conical tip 12. Clamping grips 3 are formed with conical surfaces 14 at their edges 13 which in assembly form a conical surface cooperating with the conically formed tip 12 of setscrew 4.

When setscrew 4 is loosened tubular member 15 is inserted into chamber 2. Upon the advancement of set screw 4 its conical tip 12 will cooperate with conical surfaces 14 of grips 3 so as press one grip away from another. Due to this pressure circular surfaces 8 of clamping grips 3 opposite to respective surfaces 14 will be pressed toward the interior of chamber 2 so as to clamp tubular member 15 in chamber 2. Eventually manufacturing uneveness of tube 15, such as non-circular or conical periphery thereof will be compensated by the overhung position of clamping grips 3 mounted in assembly by pins 9 because clamping grips 3 are able to pivot or tilt in each direction, particularly in the axial direction. The non-circular or conical periphery of the tube end will be compensated by clamping grips 3 by the surface contact pressure exerted on the tube along approximately the entire length thereof. Therefore, damage and weakening of tubes 15 due to local limited loads will be totally prevented.

It will be understood that each of the elements described above, or two or more together, may also find a useful application in other types of tubular joints for fastening skeleton elements of artificial limbs differing from the types described above.

While the invention has been illustrated and described as embodied in a tubular joint, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A tubular coupling for receiving and fastening a skeleton tubular element of an artificial limb, comprising a tubular member having a chamber to receive the tubular element therein and further formed with a recess defined by inner walls of the coupling conically inclined towards each other; two clamping grips positioned in said recess, said grips having circular surfaces corresponding to the other surface of the tubular element to be received in said chamber; and an adjusting screw insertable into the coupling to press against said clamping grips so that said grips abut against said inner inclined walls and said circular surfaces abut against the tubular element received in said chamber to clamp it in position, said clamping grips being positioned in said tubular member so that they are pivotable in the direction of an axis of the tubular member, said clamping grips being overhung in said recess, said adjusting screw being inserted into said tubular member at the heights thereof corresponding to positions of pivot points of said clamping grips, said clamping grips each having a curved surface corresponding to the respective inclined inner wall of the tubular member, said grips being each connected to the tubular member at a point extending approximately in the middle of a curvature defining said curved surface.

2. The coupling as defined in claim 1, further including pins connecting said clamping grips to said tubular member, said clamping grips being adjustable in position by a hand manipulation of said adjusting screw.

3. The coupling as defined in claim 2, wherein said clamping grips each has an inclined surface opposite to the circular surface thereof so that two clamping grips inserted into said recess form a conical surface, said adjusting screw having a conical tip cooperating with said conical surface upon advancing of said screw towards said chamber.

* * * * *